US009788896B2

(12) United States Patent
Cronin et al.

(10) Patent No.: US 9,788,896 B2
(45) Date of Patent: Oct. 17, 2017

(54) RADIATION APPLICATOR AND METHOD OF RADIATING TISSUE

(75) Inventors: Nigel Cronin, Lane Bath (GB); Maria J. Boix, Bath (GB)

(73) Assignee: AngioDynamics, Inc.

( * ) Notice: Subject to any disclaimer, the term of this patent is extended or adjusted under 35 U.S.C. 154(b) by 2085 days.

(21) Appl. No.: 10/577,414

(22) PCT Filed: Jul. 1, 2005

(86) PCT No.: PCT/EP2005/007103
§ 371 (c)(1),
(2), (4) Date: Apr. 26, 2006

(87) PCT Pub. No.: WO2006/002943
PCT Pub. Date: Jan. 12, 2006

(65) Prior Publication Data
US 2008/0275436 A1   Nov. 6, 2008

(30) Foreign Application Priority Data
Jul. 2, 2004   (GB) .................................. 0414976.1

(51) Int. Cl.
*A61B 18/18*   (2006.01)
*A61B 18/00*   (2006.01)

(52) U.S. Cl.
CPC .......... *A61B 18/18* (2013.01); *A61B 18/1815* (2013.01); *A61B 2018/00023* (2013.01); *A61B 2018/1838* (2013.01)

(58) Field of Classification Search
CPC ........ A61B 2018/1838; A61B 18/1815; A61B 2018/183

(Continued)

(56) References Cited

U.S. PATENT DOCUMENTS 3,065,752 A   11/1962 Fritz et al.
3,461,261 A   8/1969 Lewis et al.
(Continued)

FOREIGN PATENT DOCUMENTS

AU   2003267607 A1   5/2004
CA   2339277 A1   11/1999
(Continued)

OTHER PUBLICATIONS

"Notification of Transmittal of the International Search Report and the Written Opinion of the International Searching Authority, or the Declaration," International Filing Date: Jul. 7, 2005, International Application No. PCT/EP2005/007103, Applicant: Microsulis Limited, Date of Mailing: Oct. 11, 2005, pp. 1-13.
(Continued)

*Primary Examiner* — Ronald Hupczey, Jr.
(74) *Attorney, Agent, or Firm* — Peter Flora, Esq.

(57) ABSTRACT

A radiation applicator (102) for applying electromagnetic radiation to tissue, comprising: an axial central conductor (124) adapted to be coupled to a source of electromagnetic radiation and defining an axis; an elongate dielectric member (126), the dielectric member surrounding at least part of said central conductor along an axial length thereof; a metal ferrule (106), the ferrule being attached to the dielectric member and surrounding a portion of the central conductor and extending parallel thereto along a length thereof. The ferrule and the dielectric member have respective elongate cooperating surfaces and wherein the ferrule and the dielectric member are fixed to each other with said cooperating surfaces in close abutment, thereby providing a rigid structure.

12 Claims, 8 Drawing Sheets

(58) Field of Classification Search
USPC .............................. 606/32–50; 607/154, 156
See application file for complete search history.

(56) References Cited

U.S. PATENT DOCUMENTS

| | | | |
|---|---|---|---|
| 3,871,359 A | 3/1975 | Pacela | |
| 4,446,874 A | 5/1984 | Vaguine | |
| 4,476,363 A | 10/1984 | Berggren et al. | |
| 4,557,272 A | 12/1985 | Carr et al. | |
| 4,612,940 A * | 9/1986 | Kasevich | A61B 18/18 219/712 |
| 4,676,258 A | 6/1987 | Inokuchi et al. | |
| 4,891,483 A | 1/1990 | Kikuchi et al. | |
| 5,227,730 A | 7/1993 | King et al. | |
| 5,364,392 A | 11/1994 | Warner et al. | |
| 5,370,644 A | 12/1994 | Langberg | |
| 5,458,597 A | 10/1995 | Edwards et al. | |
| 5,536,267 A | 7/1996 | Edwards et al. | |
| 5,540,737 A | 7/1996 | Fenn | |
| 5,620,479 A | 4/1997 | Diederich | |
| 5,628,770 A * | 5/1997 | Thome | A61B 18/18 607/101 |
| 5,630,426 A | 5/1997 | Eggers et al. | |
| 5,683,384 A | 11/1997 | Gough et al. | |
| 5,728,143 A | 3/1998 | Gough et al. | |
| 5,735,847 A | 4/1998 | Gough et al. | |
| 5,800,484 A | 9/1998 | Gough et al. | |
| 5,800,494 A * | 9/1998 | Campbell et al. | 607/116 |
| 5,807,272 A | 9/1998 | Kun et al. | |
| 5,810,742 A | 9/1998 | Pearlman | |
| 5,873,849 A | 2/1999 | Bernard | |
| 5,904,709 A * | 5/1999 | Arndt et al. | 607/101 |
| 6,009,347 A | 12/1999 | Hofmann | |
| 6,016,452 A | 1/2000 | Kasevich | |
| 6,027,502 A | 2/2000 | Desai | |
| 6,047,216 A * | 4/2000 | Carl et al. | 607/101 |
| 6,050,994 A | 4/2000 | Sherman | |
| 6,066,134 A | 5/2000 | Eggers et al. | |
| 6,106,524 A | 8/2000 | Eggers et al. | |
| 6,134,460 A | 10/2000 | Chance | |
| 6,134,476 A | 10/2000 | Arndt et al. | |
| 6,200,314 B1 | 3/2001 | Sherman | |
| 6,223,085 B1 * | 4/2001 | Dann et al. | 607/101 |
| 6,223,086 B1 | 4/2001 | Carl et al. | |
| 6,287,302 B1 | 9/2001 | Berube | |
| 6,296,636 B1 | 10/2001 | Cheng et al. | |
| 6,298,726 B1 | 10/2001 | Adachi et al. | |
| 6,436,072 B1 | 8/2002 | Kullas et al. | |
| 6,478,793 B1 | 11/2002 | Cosman et al. | |
| 6,485,487 B1 | 11/2002 | Sherman | |
| 6,488,678 B2 | 12/2002 | Sherman | |
| 6,496,738 B2 * | 12/2002 | Carr | 607/101 |
| 6,497,704 B2 | 12/2002 | Ein-Gal | |
| 6,514,251 B1 * | 2/2003 | Ni et al. | 606/41 |
| 6,558,378 B2 | 5/2003 | Sherman et al. | |
| 6,616,657 B2 | 9/2003 | Simpson et al. | |
| 6,635,055 B1 | 10/2003 | Cronin | |
| 6,673,070 B2 | 1/2004 | Edwards et al. | |
| 6,706,040 B2 * | 3/2004 | Mahon et al. | 606/41 |
| 6,712,811 B2 | 3/2004 | Underwood et al. | |
| 6,723,094 B1 | 4/2004 | Desinger | |
| 6,770,070 B1 | 8/2004 | Balbierz | |
| 6,869,430 B2 | 3/2005 | Balbierz et al. | |
| 6,962,587 B2 | 11/2005 | Johnson et al. | |
| 7,008,421 B2 | 3/2006 | Daniel et al. | |
| 7,311,703 B2 * | 12/2007 | Turovskiy et al. | 606/33 |
| 7,488,292 B2 | 2/2009 | Adachi | |
| 7,553,309 B2 | 6/2009 | Buysse et al. | |
| 7,699,842 B2 | 4/2010 | Buysse et al. | |
| 7,776,035 B2 | 8/2010 | Rick et al. | |
| 7,846,108 B2 | 12/2010 | Turovskiy et al. | |
| 7,875,025 B2 | 1/2011 | Cockburn et al. | |
| 8,062,290 B2 | 11/2011 | Buysse et al. | |
| 8,073,550 B1 | 12/2011 | Spertell | |
| 8,182,477 B2 | 5/2012 | Orszulak et al. | |
| 8,377,057 B2 | 2/2013 | Rick et al. | |
| 8,398,626 B2 | 3/2013 | Buysse et al. | |
| 8,512,330 B2 | 8/2013 | Epstein et al. | |
| 8,579,902 B2 | 11/2013 | Bleich et al. | |
| 8,586,897 B2 | 11/2013 | Cronin | |
| 8,613,745 B2 | 12/2013 | Bleich | |
| 8,617,163 B2 | 12/2013 | Bleich | |
| 8,647,346 B2 | 2/2014 | Bleich et al. | |
| 8,652,138 B2 | 2/2014 | Bleich et al. | |
| 8,801,626 B2 | 8/2014 | Sun et al. | |
| 8,853,600 B2 | 10/2014 | Spertell | |
| 9,101,386 B2 | 8/2015 | Wallace et al. | |
| 9,113,888 B2 | 8/2015 | Orszulak et al. | |
| 9,247,952 B2 | 2/2016 | Bleich et al. | |
| 2001/0008966 A1 | 7/2001 | Arndt et al. | |
| 2002/0077627 A1 | 6/2002 | Johnson et al. | |
| 2002/0161361 A1 | 10/2002 | Sherman et al. | |
| 2003/0088242 A1 | 5/2003 | Prakash et al. | |
| 2003/0100894 A1 | 5/2003 | Mahon et al. | |
| 2003/0109862 A1 | 6/2003 | Prakash et al. | |
| 2004/0049254 A1 | 3/2004 | Longo | |
| 2004/0204679 A1 | 10/2004 | Visconti et al. | |
| 2004/0215185 A1 | 10/2004 | Truckai et al. | |
| 2004/0267340 A1 | 12/2004 | Cioanta et al. | |
| 2005/0015081 A1 | 1/2005 | Turovskiy et al. | |
| 2005/0033276 A1 | 2/2005 | Adachi | |
| 2005/0107781 A1 | 5/2005 | Ostrovsky et al. | |
| 2005/0245920 A1 * | 11/2005 | Vitullo et al. | 606/33 |
| 2006/0151485 A1 | 7/2006 | Cronin | |
| 2006/0217704 A1 | 9/2006 | Cockburn et al. | |
| 2006/0293734 A1 | 12/2006 | Scott et al. | |
| 2007/0191825 A1 | 8/2007 | Cronin et al. | |
| 2007/0203551 A1 | 8/2007 | Cronin et al. | |
| 2008/0275436 A1 | 11/2008 | Cronin et al. | |
| 2008/0314894 A1 | 12/2008 | Cronin | |
| 2009/0240247 A1 | 9/2009 | Rioux et al. | |
| 2010/0292686 A1 | 11/2010 | Rick et al. | |
| 2011/0230874 A1 | 9/2011 | Epstein et al. | |
| 2014/0042154 A1 | 2/2014 | Cronin | |
| 2014/0081255 A1 | 3/2014 | Johnson et al. | |
| 2015/0066020 A1 | 3/2015 | Epstein et al. | |
| 2016/0000505 A1 | 1/2016 | Cronin | |

FOREIGN PATENT DOCUMENTS

| | | |
|---|---|---|
| EP | 0 105 677 A1 | 4/1984 |
| EP | 0294854 A2 | 12/1988 |
| GB | 2074826 A | 11/1981 |
| GB | 2387544 A | 10/2003 |
| GB | 2387544 A | 10/2003 |
| GB | 2406521 A | 4/2005 |
| GB | 2415630 A | 1/2006 |
| GB | 2406521 B | 5/2007 |
| JP | 2002109971 A | 4/2002 |
| WO | WO-99/07297 | 2/1999 |
| WO | WO-00/09208 A | 2/2000 |
| WO | WO-2004/033039 A | 4/2004 |
| WO | WO-2005/011049 A | 2/2005 |
| WO | 2006002943 A1 | 1/2006 |

OTHER PUBLICATIONS

Maybody, An Overview of Image-Guided Percutaneous Ablation of Renal Tumors, Seminars in Interventional Radiology/vol. 27, No. 3, 2010, pp. 261-267.

Carmi, et al, Combination Percutaneous and Intraarterial Therapy for the Treatment of Hepatocellular Carcinoma: A Review, Semin Intervent Radiol 2010, 27:296-301.

Saldanha, et al, Current Tumor Ablation Technologies: Basic Science and Device Review, Semin Intervent Radiol 2010, 27:247-254.

Kurup, et al, Image-Guided Percutaneous Ablation of Bone and soft Tissue Tumors, Semin Intervent Radiol 2010, 27:276-284.

McCarley, et al, Percutaneous Ablation of Hepatic Tumors, Semin Intervent Radiol 2010, 27: 255-260.

International Search Report PCT-GB-04-002620 ISR, dated Jan. 10, 2004.

(56) References Cited

OTHER PUBLICATIONS

International Search Report PCT-EP-05-007103 WOSA, dated Feb. 1, 2007.
International Search Report PCT-GB-99-01398 WOSA, dated Feb. 2, 2000.
International Search Report PCT-EP-06-012144 IPRP, dated Feb. 5, 2008.
International Search Report PCT-EP-05-007553 IPRP, dated Feb. 11, 2006.
International Search Report PCT-GB-94-01565 IPER, dated Feb. 11, 1995.
International Search Report PCT-GB-10-051625 ISR, dated Mar. 5, 2011.
International Search Report PCT-EP-06-012144 ISR, dated Mar. 7, 2007.
International Search Report PCT-GB-99-01398 ISR, dated Mar. 9, 1999.
International Search Report PCT-GB-99-01400 ISR, dated Mar. 9, 1999.
International Search Report PCT-GB-11-051735 WOSA, dated Apr. 5, 2013.
International Search Report PCT-EP-05-007553 ISR, dated Apr. 10, 2005.
International Search Report PCT-GB-10-051625 WOSA, dated Jun. 4, 2012.
International Search Report PCT-GB-11-051735 IPRP, dated Jul. 5, 2013.
International Search Report PCT-GB-99-01398 IPER, dated Jul. 8, 2000.
International Search Report PCT-EP-05-007103 IPRP, dated Jan. 9, 2007.
International Search Report 09155664 ESR, dated Jun. 9, 2009.
International Search Report PCT-GB-09-050113 IPRP, Aug. 10, 2010.
International Search Report PCT-GB-10-051625 IPRP, dated Apr. 11, 2012.
International Search Report PCT-GB-99-001398 ISR, dated Nov. 11, 1999.
International Search Report PCT-GB-99-001400 ISR, dated Nov. 11, 1999.
International Search Report PCT-EP-05-007103 ISR, dated Jan. 12, 2006.
International Search Report PCT-GB-03-04082 IPER, dated Nov. 12, 2004.
International Search Report PCT-GB-11-051735 ISR, dated Dec. 15, 2011.
International Search Report 04815540 SESR, dated Jan. 21, 2010.
International Search Report PCT-GB-00-00682 IPRP, dated May 21, 2001.
International Search Report PCT-GB-04-002620 IPRP, dated Jul. 21, 2005.
International Search Report PCT-GB-03-004082 ISR, dated Apr. 22, 2004.
International Search Report PCT-GB-00-00682 ISR, dated May 24, 2000.
International Search Report PCT-GB-09-050113 ISR, dated May 25, 2009.
International Search Report PCT-US-04-043477 IPRP, dated Jun. 26, 2006.
International Search Report PCT-US-04-043477 ISR, dated Aug. 26, 2005.
International Search Report, PCT-GB-94-01565 ISR, dated Nov. 28, 1994.

* cited by examiner

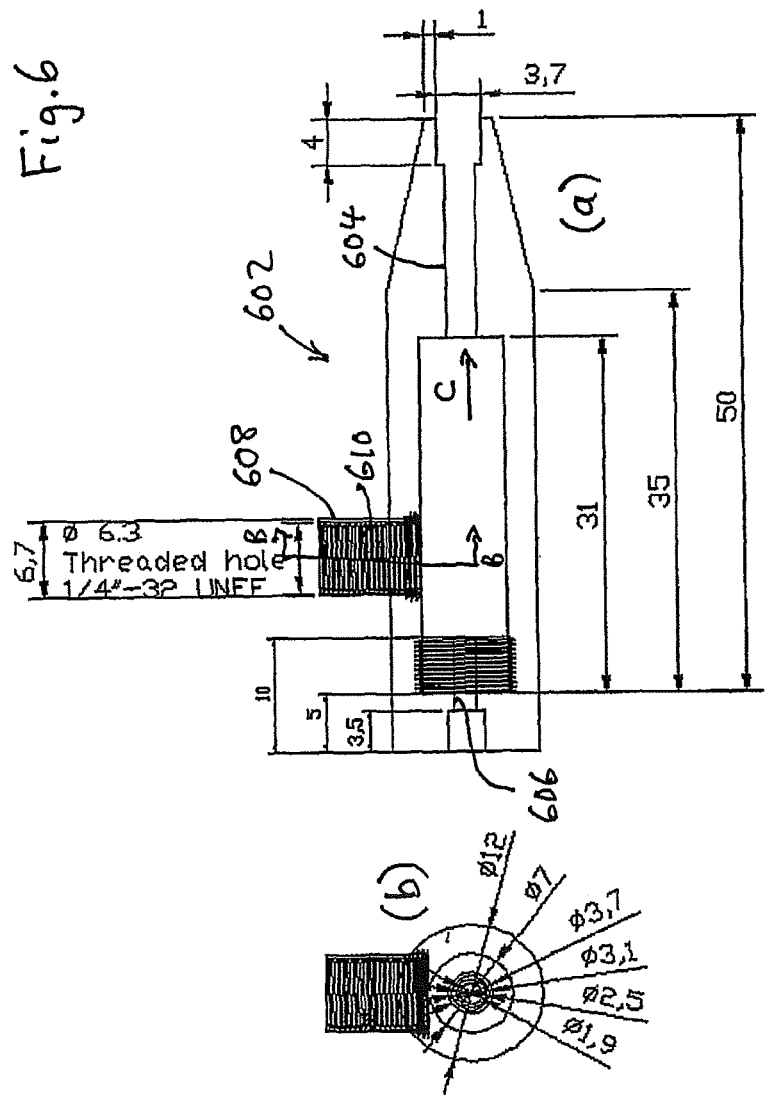
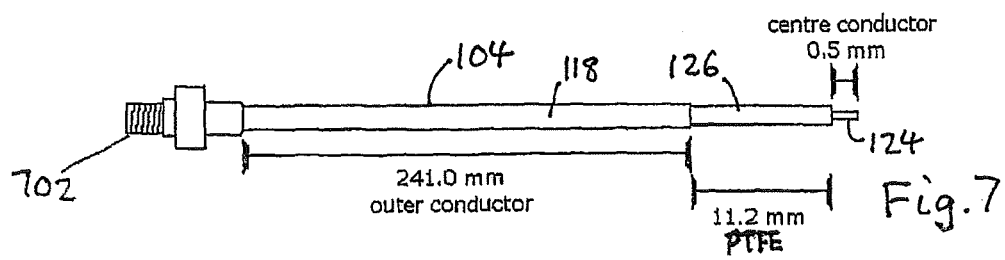

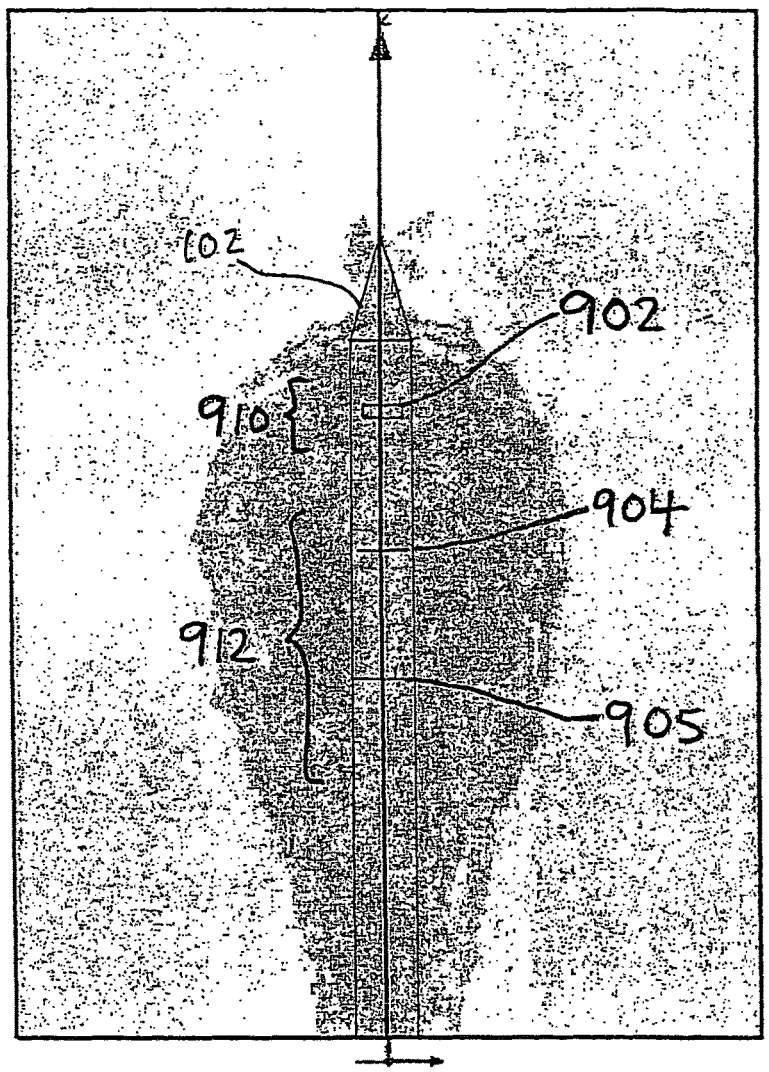
Fig. 9(b)
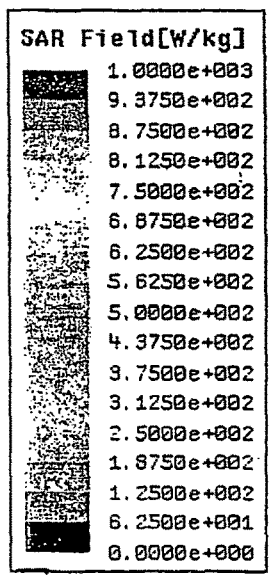

RADIATION APPLICATOR AND METHOD OF RADIATING TISSUE

The present invention relates to medical technology, and more particularly to a microwave radiation applicator and a method of thermal ablative treatment of tissue using radiated microwaves.

Thermal ablative therapies may be defined as techniques that intentionally decrease body tissue temperature (hypothermia) or intentionally increase body tissue temperature (hyperthermia) to temperatures required for cytotoxic effect, or other therapeutic temperatures required for a particular treatment.

The Invention is concerned with hyperthermic thermal ablative therapies. Examples of these include RF, Laser, Focussed (or Ultra-High Speed) Ultrasound, and microwave treatments.

Microwave thermal ablation relies on the fact that microwaves form part of the electromagnetic spectrum causing heating due to interaction between water molecules and the microwave radiation, the heat being used as the cytotoxic mechanism. Treatment Involves the Introduction of an applicator into the tumours. Microwaves are released from the applicator forming a field around its tip. Direct heating of the water molecules in particular occurs in the radiated microwave field produced around the applicator rather than by conduction from the probe itself. Heating is therefore not reliant on conduction through tissues and cytotoxic temperature levels are reached rapidly.

Microwave thermal ablative techniques are useful in the treatment of tumours of the liver, brain, lung, bone, etc.

U.S. Pat. No. 4,494,539 discloses a surgical operation method using microwave, characterized in that microwaves are radiated to bio-tissue from a monopolar type operating electrode attached to the Up of a coaxial cable for transmitting microwaves, and an operation of coagulation, hemostasis or transection is performed on the bio-tissue with the use of thermal energy generated from the reaction of the microwaves on the bio-tissue. The bio-tissue can be operated in an easy, safe and bloodless manner. Therefore, the method can be utilized for an operation on a parenchymatous organ having a great blood content or for coagulation or transection on a parenchymatous tumour. According to the method, there can be performed an operation on liver cancer which has been conventionally regarded as very difficult. A microwave radiation applicator is also disclosed. Possible treatments also include those of tumours of the liver, spleen and ovary.

U.S. Pat. No. 6,325,796 discloses a microwave ablation assembly and method, including a relatively thin, elongated probe having a proximal access end and an opposite distal penetration end adapted to penetrate into bio-tissue. The probe defines an insert passage extending therethrough from the access end to the penetration end thereof. An ablation catheter includes a coaxial transmission line with an antenna device coupled to a distal end of the transmission line for generating an electric field sufficiently strong to cause tissue ablation. The coaxial transmission line includes an inner conductor and an outer conductor separated by a dielectric material medium. A proximal end of the transmission line is coupled to a microwave energy source. The antenna device and the transmission line each have a transverse cross-sectional dimension adapted for sliding receipt through the insert passage while the elongated probe is positioned in the bio-tissue. Such sliding advancement continues until the antenna device is moved to a position beyond the penetration end and further into direct contact with the bio-tissue.

However, a drawback with existing techniques include the fact that they are not optimally mechanically configured for insertion into, and perforation of, the human skin, for delivery to a zone of soft tissue to be treated. Typically, known radiation applicator systems do not have the heightened physical rigidity that is desirable when employing such techniques.

In addition, some radiation applicators made available heretofore do not have radiation emitting elements creating a microwave field pattern optimised for the treatment of soft tissue tumours and, e.g., have through having a simple monopolar design.

Also, given the power levels employed in some applicators/treatments, there can be problems of unwanted burning of non-target, healthy tissue due to the very high temperatures reached by the applicator or components attached thereto.

Further, although small diameter applicators are known, and liquid cooling techniques have been used, there has been difficulty in designing a small diameter device with sufficient cooling in applications employing power levels required to deal with soft tissue tumours.

There is a need for methods of treatment of soft tissue tumours, and for radiation applicators, that overcome any or all of the aforementioned problems of prior art techniques and provide improved efficacy.

The present invention provides a radiation applicator for applying electromagnetic radiation to tissue, comprising a conductor coupled to a source of electromagnetic radiation; and a dielectric member adapted to deliver electromagnetic energy of a predetermined intensity pattern into the tissue.

Preferably, the radiation applicator comprises: axial central conductor coupled to a source of electromagnetic radiation; an elongate dielectric member, the dielectric member surrounding at least part of said central conductor along an axial length thereof; an elongate metal ferrule, the ferrule surrounding the central conductor and extending parallel thereto along a length thereof.

According to another aspect of the invention the ferrule and the dielectric member have cooperating surfaces and wherein the ferrule and the dielectric member are fixed to each other with the cooperating surfaces in close abutment; thereby providing a rigid structure.

In another aspect of the invention, the radiation applicator further comprises: a tuning conductor, attached to the central conductor and in electrical contact therewith; wherein the shape and dimensions of the tuning conductor, and the shape and dimensions of the dielectric member and/or the dielectric properties thereof, are predetermined whereby a radiating dipole is formed, in use, for radiating electromagnetic energy in at least a radial direction from said dielectric member.

In another aspect of the invention, the radiation applicator further comprises: an elongate metal tube; wherein the ferrule is fixedly attached on opposing respective sides thereof to the dielectric member and to the metal tube; and wherein the central conductor is electrically coupled to a cable extending within the metal tube, an elongate annular space being defined between the cable and the metal tube so as to permit the passage of cooling fluid to at least the ferrule.

In another aspect of the invention there is provided a radiation applicator for applying electromagnetic radiation to tissue, comprising: an axial central conductor coupled to a source of electromagnetic radiation; an elongate dielectric member, the dielectric member surrounding at least part of said central conductor along an axial length thereof; an elongate metal ferrule, the ferrule surrounding the central conductor and extending parallel thereto and along a length thereof; an elongate metal tube surrounding a portion of the central conductor remote from the part surrounded by the dielectric member; wherein the ferrule is fixedly attached on opposing respective sides thereof to the dielectric member and to the metal tube; and wherein the central conductor comprises the inner conductor of a cable extending within the metal tube, an elongate annular space being defined between the cable and the metal tube so as to permit the passage of cooling fluid to at least the ferrule.

The present invention further provides a method of treating target tissue, such as a tumour, the tumor target tissue being formed of, and/or being embedded within, soft tissue, comprising: inserting a radiation applicator into the target tissue, the radiation applicator being according to any of the embodiments described herein; supplying electromagnetic energy to the applicator, thereby radiating electromagnetic energy into said target tissue.

Embodiments of the invention will now be described, by way of example, with reference to the accompanying drawings, in which:

FIG. 6 illustrates (a) an axial cross-section, and (b) a transverse cross-section, of a handle section that may be attached to the metal tube in the radiation applicator of FIG. 1;

FIG. 7 illustrates the portion of coaxial cable that passes through the tube, in the radiation applicator of FIG. 1;

In the following description, like references are used to denote like elements, and where dimensions are given, these are in mm. Further, it will be appreciated by persons skilled in the art that the electronic systems employed, in accordance with the present invention, to generate, deliver and control the application of radiation to parts of the human body may be as described in the art heretofore. In particular, such systems as are described in commonly owned published international patent applications WO95/04385, WO99/56642 and WO00/49957 may be employed (except with the modifications described hereinafter): full details of these systems have been omitted from the following for the sake of brevity.

Figure 1:
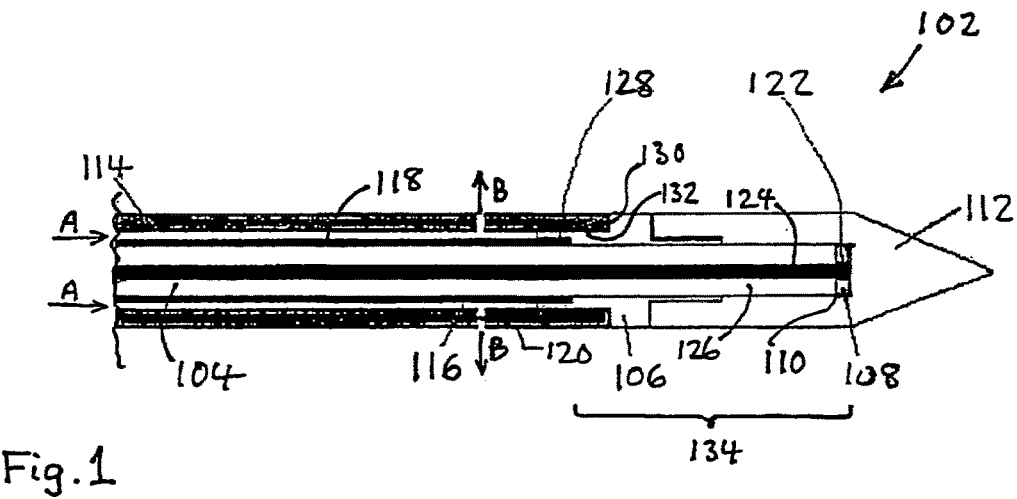
FIG. 1 is a schematic partial cross-sectional view of a radiation applicator in accordance with one embodiment of the Invention.

FIG. 1 is a schematic partial cross-sectional view of a radiation applicator in accordance with one embodiment of the invention. The radiation applicator, generally designated 102, includes a distal end portion of a coaxial cable 104 that is used to couple to a source (not shown) of microwaves, a copper ferrule 106, a tuning washer 108 attached on the end 110 of the Insulator part of the coaxial cable 104, and a tip 112. Preferably, the applicator 102 further includes a metal tube 114: this tube 114 is rigidly attached to the ferrule 106; and, as discussed further hereinafter, and annular space 116 is defined between the outer conductor 118 of the cable 104 and the Inner surface of the tube 114, enabling cooling fluid to enter (in the direction of arrows A), contact the heated parts of the applicator 102 and exit in the direction of arrows B through radial holes 120 in the tube 114, thereby extracting heat energy from the device.

In assembly of the applicator 102, the washer 108 is soldered to a small length 122 of the central conductor 124 of the cable 104 that extends beyond the end 110 of the insulator 126 of the cable 104. The ferrule 106 is soldered to a small cylindrical section (indicated as 128) of the outer conductor 118 of the cable 104. Then, the tube 114, which is preferably stainless steel, but may be made of other suitable materials, such as titanium (or any other medical grade material), is glued to the ferrule 106 by means of adhesive (such as Loctite 638 retaining compound) at the contacting surfaces thereof, indicated at 130 and 132. The tip 112 is also glued, using the same adhesive, on the inner surfaces thereof, to corresponding outer surfaces of the ferrule 106 and the cable's insulation 126.

When assembled, the applicator 102 forms a unitary device that is rigid and stable along its length, which may be of the order of 25 or so centimeters when the tube 114 is included, making it suitable for insertion into various types of soft tissue. The space 116 and holes 120 enable cooling fluid to extract heat from the applicator 102 through contact with the ferrule 106, the outer conductor 118 of the cable 104 and the end of the tube 114. The ferrule 106 assists in assuring the applicator's rigidity. The exposed end section 134 of cable 104 (from which the outer conductor 118 has been removed), in conjunction with the dielectric tip 112, being fed by a source of radiation of predetermined frequency, operate, in use, as a radiating antenna for radiating microwaves into tissue for therapeutic treatment. The applicator 102 operates, in use, as a dipole antenna rather than a monopole device, resulting in an emitted radiation pattern that is beneficial, due to its spherical direct heated area (larger burn), for the treatment of certain tissues, such as malignant or tuimorous tissue.

Figure 2:
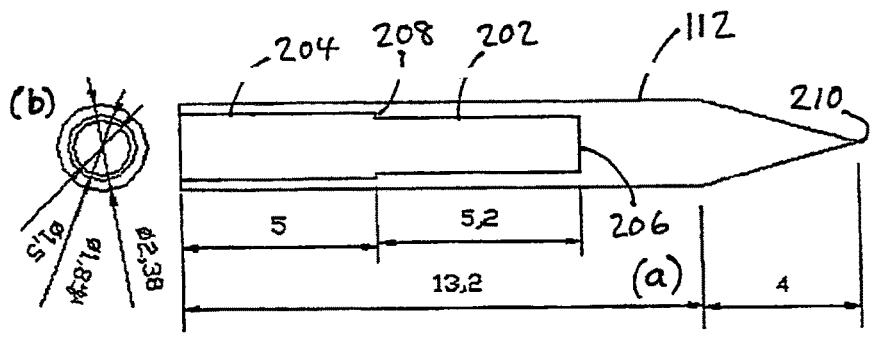
FIG. 2 shows (a) an axial cross-section, and (b) an end elevation of the radiating tip part of the radiation applicator of FIG. 1.

FIG. 2 shows (a) an axial cross-section and (b) an end elevation, of the radiating tip part 112 of the radiation applicator of FIG. 1 (in each case, the dimensions are given in mm). As can be seen, the tip 112 has inner cylindrical walls 202, 204, and abutting walls 206, 208, for receiving and abutting the washer 108 and ferrule 106 respectively, during assembly. Suitably, the tip 112 is made of zirconia ceramic alloy. More preferably, it is a partially stabilised zirconia (PSZ) having yttria as the stabilising oxidising agent. Even more preferably, the tip 112 is made of Technox 2000 (available from Dynamic Ceramic), a PSZ having a very fine uniform grain compared to other PSZs, and with a dielectric constant (k) of 25. Appropriate choice of dielectric material assists in determining the properties of the radiated microwave energy (field).

It will be noted that the transverse dimensions are relatively small: in the described embodiment the diameter is less than or equal to 2.4 mm; and the tip 112 is designed to have dimensions, and be formed of the specified material, so as to perform effective tissue ablation at the operating microwave frequency, in this case 2.45 GHz. The 2.4 mm diameter device is thus well adapted for insertion into, and treatment of, cancerous and/or non-cancerous tissue of the liver, brain, lung, veins, bone, etc.

The end 210 of the tip 112 is formed by conventional grinding techniques performed in the manufacture of the tip 112. The end 210 may be formed as a fine point (like a needle or pin), or it may be formed with an end blade (e.g. like a chisel), i.e. having a transverse dimension of elongation. The latter configuration has the benefit of being well suited to forcing the tip 112 into or through tissue, i.e. to perforate or puncture the surface (e.g. skin) of tissue.

In use, the tip 112 is preferably coated with a non-stick layer such as silicone or paralene, to facilitate movement relative to tissue.

Figure 3:
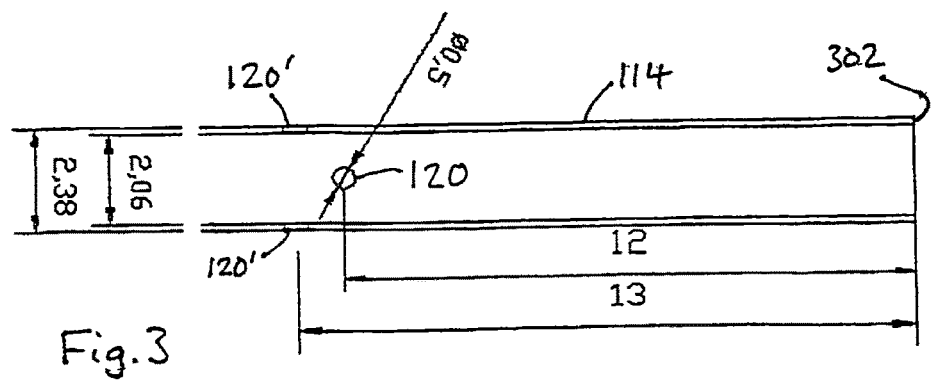
FIG. 3 shows a partial transverse cross-section of the metal pipe part of the radiation applicator of FIG. 1.

FIG. 3 shows a partial transverse cross-section of the metal pipe 114 part of the radiation applicator of FIG. 1. The tube 114 is suitably made of stainless steel (specifically 13 gauge thin wall 304 welded hard drawn (WHD) stainless steel tube). In this embodiment, the tube 114 is some 215 mm in length: only the end section that is attached to the ferrule 105 is illustrated in detail in FIG. 3.

As can be seen, in this case, two sets of holes 120, 120' are provided at 12 and 13 mm, respectively, from the end 302 of the tube 114. These radial holes 120, 120', as mentioned, permit the exit of cooling fluid. Although two sets of holes are shown, 1, 3, 4 or more sets of holes may be provided, in variants of the illustrated embodiment in addition, although two holes per set are shown, 3, 4 5, or more holes per set may be provided, so long as the structural rigidity of the tube 114 is not compromised. In this embodiment, the holes 120, 120' are of 0.5 mm diameter, but it will be appreciated that this diameter may be quite different, e.g. any thing in the range 0.1 to 0.6 mm, depending on the number of sets of holes and/or the number of holes per set, in order to provide effective flow rate. Although the illustrated distance from the end 302 is 12 or 13 mm, in alternative embodiments this may be any thing from 3 mm to 5 cm from the end 302, in order to control the length of track that requires cauterisation.

Further, in an embodiment used in a different manner, the tube 114 may be omitted. In this case the treatment may comprise delivering the applicator to the treatment location (e.g. tuimorous tissue) by suitable surgical or other techniques. For example, in the case of a brain tumour, the applicator may then be left in place inside the tumour, the access wound closed, and a sterile connector left at the skull surface for subsequent connection to the microwave source for follow-up treatment at a later date.

Figure 4:
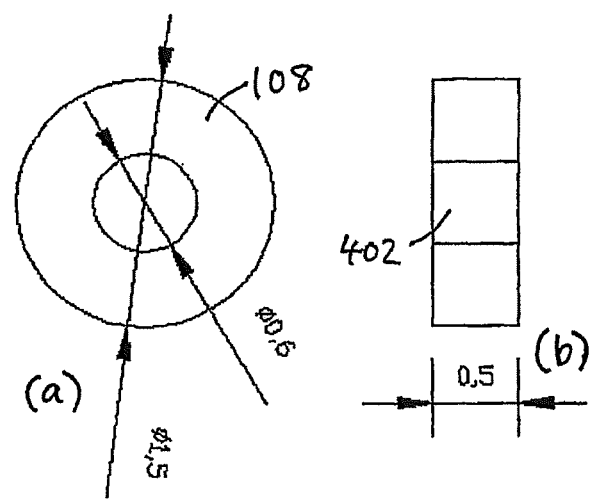
FIG. 4 shows (a) a transverse cross-section, and (b) an axial cross-section, of the tuning washer in the radiation applicator of FIG. 1.

FIG. 4 shows (a) a transverse cross-section and (b) an axial cross-section, of the tuning washer 108 in the radiation applicator 102 of FIG. 1. The washer 108 is suitably made of copper, although other metals may be used. The washer 108 has an inner cylindrical surface 402 enabling it to be soldered to the central conductor 124 of the cable 104 (see FIG. 1). Although the washer is small, its dimensions are critical. The washer tunes the applicator, which operates as a dipole radiator (radiating energy from two locations), so that more effective treatment (ablation) of tissue is effected.

Figure 5:
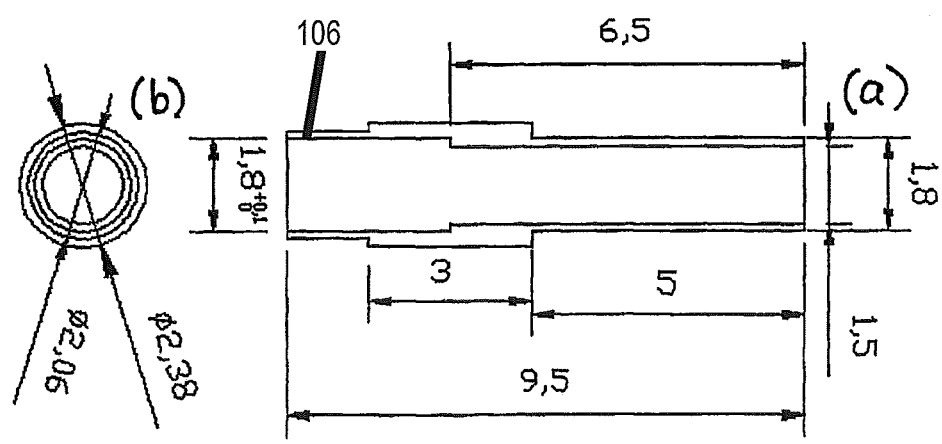
FIG. 5 shows (a) an axial cross-section, and (b) an end elevation, of the ferrule in the radiation applicator of FIG. 1.

FIG. 5 shows (a) an axial cross-section, and (b) an end elevation, of the ferrule 106 in the radiation applicator 102 of FIG. 1. The ferrule 106 is suitably made of copper, and is preferably gold plated to protect against any corrosive effects of the cooling fluid, the composition of which is discussed hereinafter. The ferrule 106 is suitably produced by conventional (e.g. CNC) machining techniques.

FIG. 6 illustrates (a) an axial cross-section and (b) a transverse cross-section at B-B of a handle section 602 that may be attached to the metal tube 114 in the radiation applicator 102 of FIG. 1. The handle section 602 is suitably stainless steel, and is preferably formed of the same material as the tube 114. The handle section includes a forward channel 604 enabling insertion of the tube 114 during assembly, and a rear channel 606 enabling insertion of the coax cable 104 during assembly. A transverse port BOB having an internal thread 610 enables the connection of a (suitably plastic) connector, for connecting to a source of cooling fluid, discussed later. Once assembled, the arrangement enables cooling fluid to pass in the direction of arrow C into the tube 114 (not shown).

FIG. 7 illustrates the portion of coaxial cable 104 that passes through the tube 114, in the radiation applicator 102 of FIG. 1. The cable 104 suitably comprises a low-loss coaxial cable such as SJS-070LL-253-Strip cable. A connector 702 (suitably SMA female type) permits connection of the cable 104 to a microwave source (not shown), or to an intermediate section of coax cable (not shown) that in turn connect to the microwave source.

Figure 8:
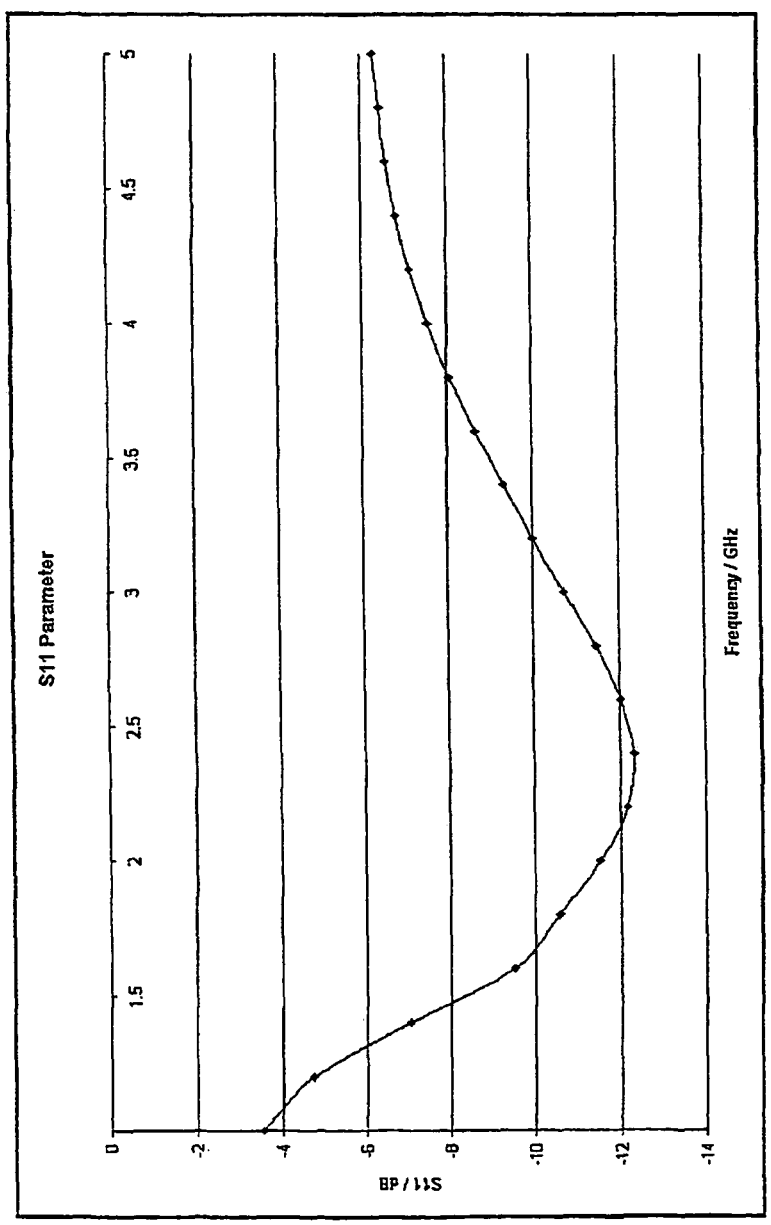
FIG. 8 is a plot of $S_{11}$ against frequency for the radiation applicator of FIG. 1.

FIG. 8 is a plot of $S_{11}$ against frequency for the radiation applicator of FIG. 1. This illustrates the ratio of reflective reflected microwave power from the interface of the applicator 102 and treated tissue to total input power to the applicator 102. As can be seen, the design of the applicator 102 causes the reflected power to be a minimum, and therefore the transmitted power into the tissue to be a maximum, at the frequency (2.45 GHz) of the delivered microwaves.

Figure 9A:
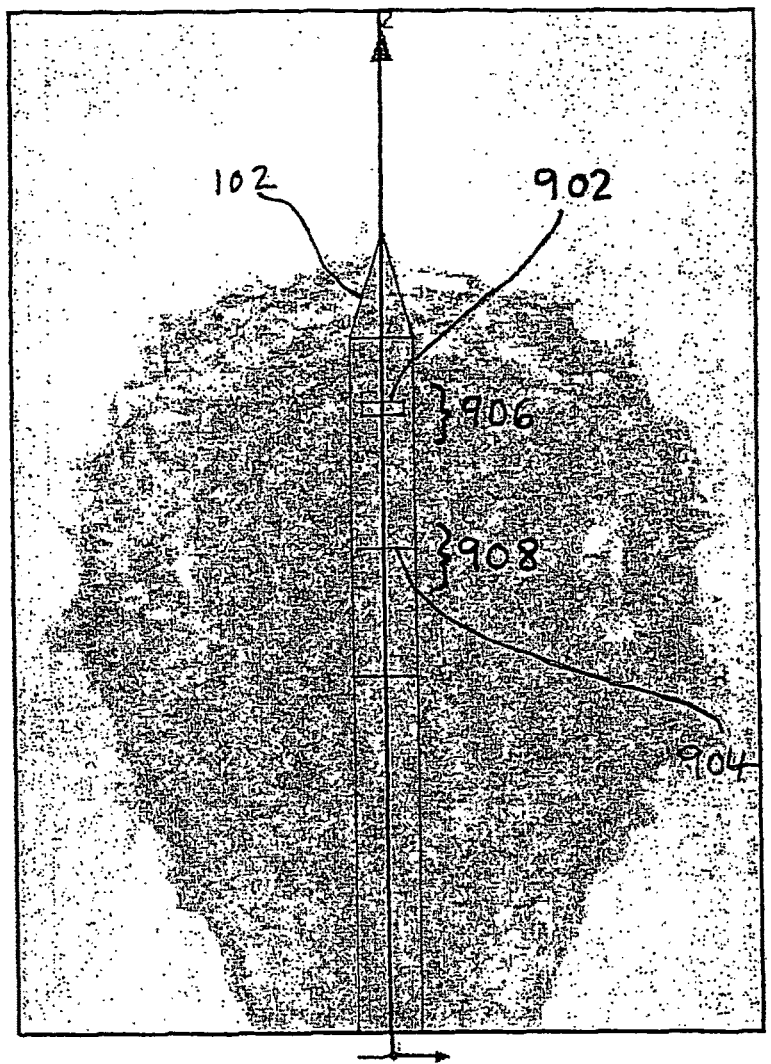
FIG. 9 illustrates (a) the E-field distribution, and (b) the SAR values, around the radiation applicator of FIG. 1, in use.

FIG. 9(*a*) shows the E-field distribution around the radiation applicator 102 of FIG. 1, in use. Darker colours adjacent the applicator 102 indicate points of higher electric field. In FIG. 9(*a*), the position of the washer 108 is indicated at 902, and the position of the tip-ferrule junction is indicated at 904. Two limited substantially cylindrical zones 906, 908, of highest electric field are thus formed around the applicator 102 at the positions 902 and 904 respectively.

FIG. 9(*b*) shows the SAR (specific absorption rate) value distribution around the radiation applicator 102 of FIG. 1, in use. Darker colours adjacent the applicator 102 indicate points of SAR. In FIG. 9(*b*), the position of the washer 108 is indicated at 902, the position of the tip-ferrule junction is indicated at 904, and the position of the ferrule-tube junction is indicated at 905. Two limited substantially cylindrical zones 910, 912, of highest SAR are thus formed around the applicator 102 at the positions 902 and between 904 and 905, respectively.

Figure 10:
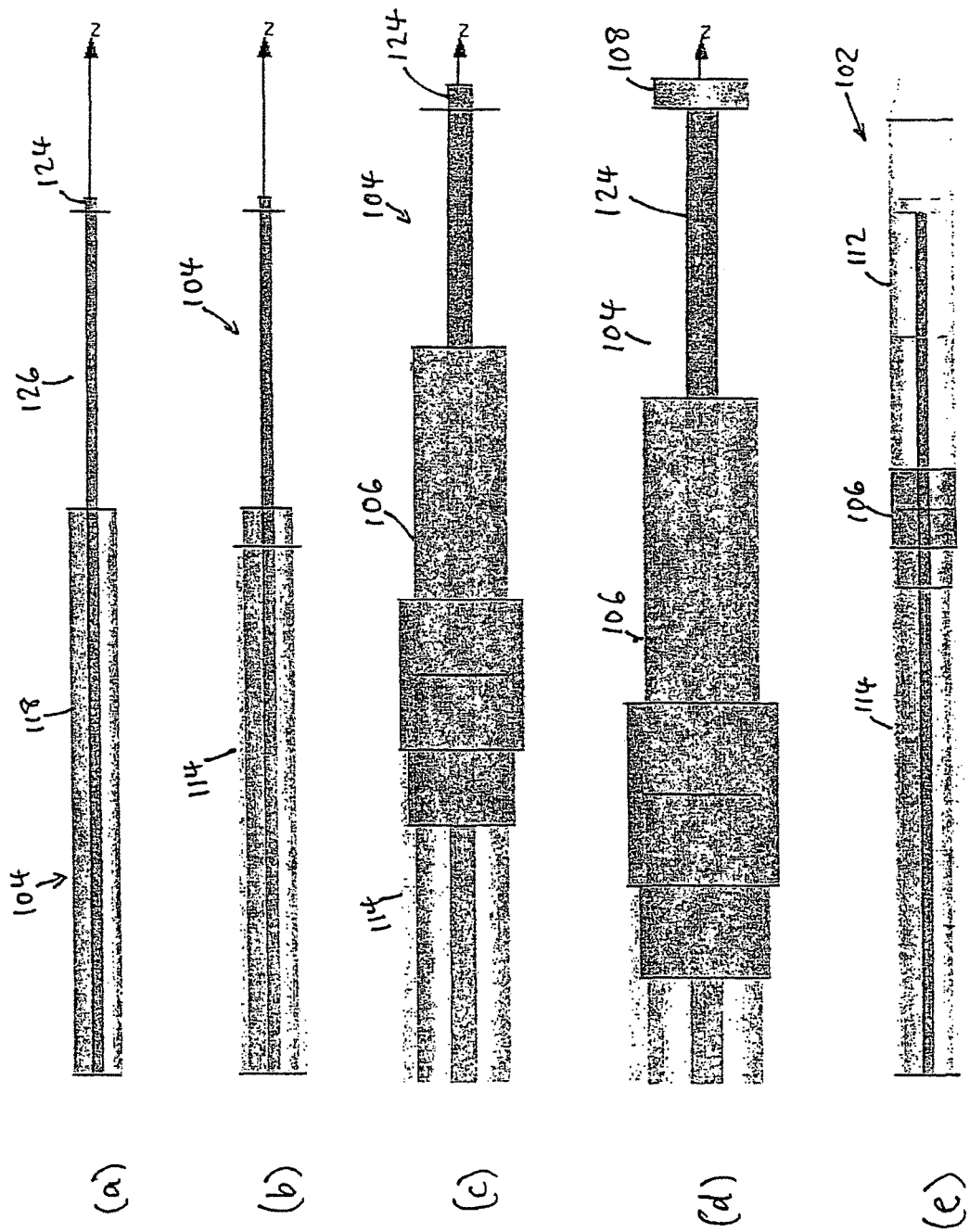
FIG. 10 shows sequentially the assembly of components to form the radiation applicator of FIG. 1.

FIG. 10 shows sequentially the assembly of components to form the radiation applicator 102 of FIG. 1. In FIG. 10(*a*), the coax cable 104 is shown, with the outer conductor 118 and the Inner insulator 126 trimmed back, as illustrated earlier in FIG. 7.

As shown in FIG. 10(*b*), the tube 114 is then slid over the cable 104. Next, the ferrule 106 is slid over the cable 104 (see FIG. 10(*c*), and fixedly attached to the tube 114 and to the cable 104, as described earlier. Then, the washer 108 is attached to the inner conductor 124 by soldering, as shown in FIG. 10(*d*). Finally, the tip 112 is slid over the cable 104 and part of the ferrule 106, and glued thereto, as described earlier; the completed applicator is shown in FIG. 10(*e*). This results in a radiator construction of great rigidity and mechanical stability.

Figure 11:
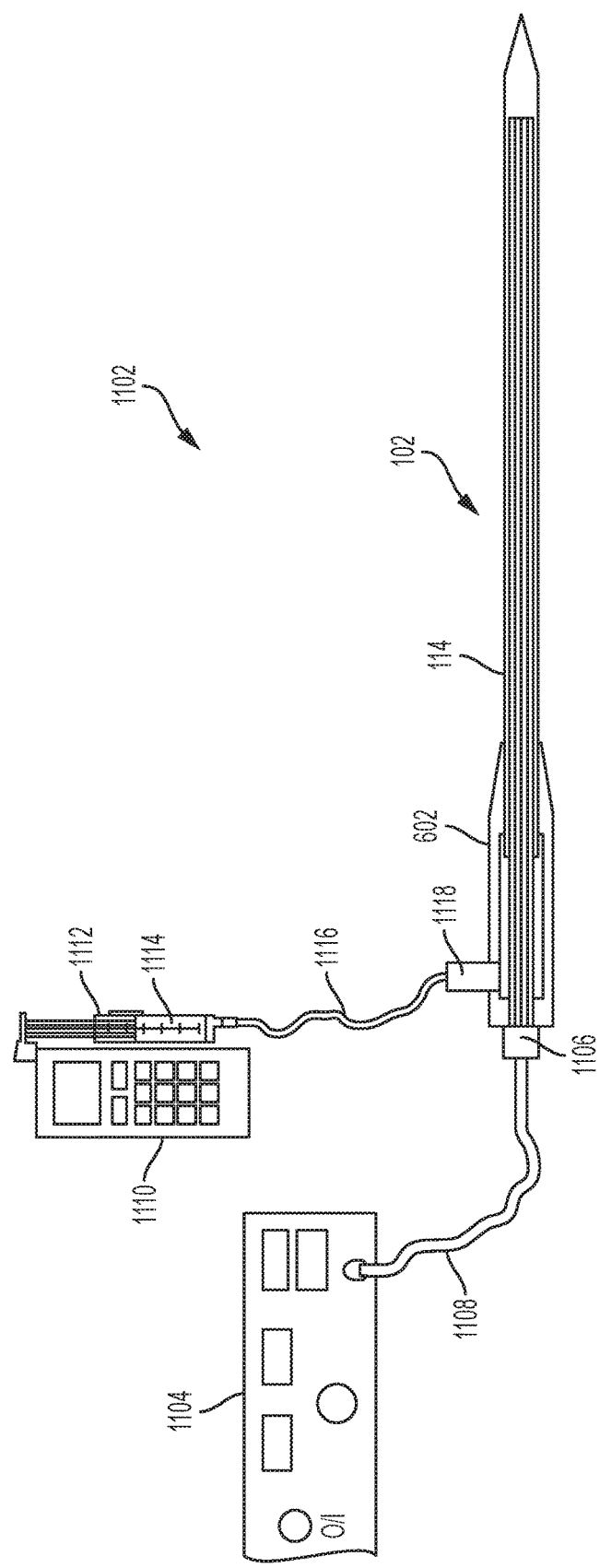
FIG. 11 schematically illustrates a treatment system employing the radiation applicator of FIG. 1.

FIG. 11 schematically illustrates a treatment system 1102 employing the radiation applicator 102 of FIG. 1. Microwave source 1104 is couple to the input connector 1106 on handle 602 by coaxial cable 1108. In this embodiment, the microwave power is supplied at up to 80 W. However this could be larger for larger size applicators (e.g. up to 200 W for 5 mm dia. applicators)

Syringe pump 1110 operates a syringe 1112 for supplying cooling fluid 1114 via conduit 1116 and connector 1118 attached to handle 602, to the interior of the handle section 602. The fluid is not at great pressure, but is pumped so as to provide a flow rate of about 1.5 to 2.0 ml/minute through the pipe 114 in the illustrated embodiment. (However, in variants of the embodiment, where an applicator is operated at higher powers, higher flow rates than this may be employed, so as to provide appropriate cooling.) Suitably, the cooling fluid is saline, although other liquids or gases may be used, such as ethanol. In certain embodiments, a cooling liquid having a secondary (cytotoxic) effect could be used, enhancing the tumour treatment. In the Illustrate embodiment, the cooling fluid 1114 exits the tube 114 (see arrows B in FIG. 1) at a temperature of the order of 10° C. higher than that at which it enters (see arrows A in FIG. 1) the tube 114. Thus, substantial thermal energy is extracted from the radiation applicator 102. The cooling fluid 1114 may, for example, enter the tube 1114 at room temperature; however, the cooling fluid 1114 may be pre-cooled to below room temperature by any suitable technique.

The methodology for use of the above-described applicator may be as conventionally employed in the treatment of various soft tissue tumours. Thus, the applicator is inserted into the body, laparoscopically, percutaneously or surgically, moved to the correct position by the user (assisted where necessary by positioning sensors and/or imaging tools, such as ultrasound) so that the tip 112 is embedded in the tissue to be treated. The microwave power is switched on, and the tissue thus ablated for a predetermined period under the control of the user. In most cases, the applicator is stationary during treatment. However, in some instances (e.g. veins), the applicator may be moved (gentle sliding motion relative to the target tissue) while the microwave radiation is being applied.

The invention claimed is:

1. A radiation applicator for applying electromagnetic radiation to tissue, comprising:
    a central conductor having a distal end and a proximal end and adapted to be coupled to a source of electromagnetic radiation;
    a dielectric tip member having a distal end and a proximal end;
    an outer conductor having a distal end and a proximal end, and outer tube having a distal end including a distal most end, and a proximal end, the distal most end of the outer tubing ending proximal to a distal most end of the applicator, the outer tube coaxially surrounding the outer conductor such that a gap is formed between the outer conductor and the outer tube;
    the gap extends from a proximal end of the applicator to a ferrule, the ferrule having a distal end including a distal most end, and a proximal end, the distal most end of the ferrule extending distally beyond the distal most end of the outer tube for a selected distance, the ferrule having a first surface, a second surface, a third surface, the first surface of the ferrule extending coaxially along the outer conductor and the central conductor, the second surface of the ferrule coaxially extends along the distal end of the central conductor, and the third surface of the ferrule coaxially extends between the distal end of the outer conductor and the distal end of the outer tube, the ferrule is spaced between the outer conductor and the outer tube thereby sealing the gap such that the proximal end of the ferrule prevents a cooling fluid from contacting a dipole antenna;
    a tuning conductor attached to the distal end of the central conductor, the tuning conductor is in electrical contact with the central conductor;
    the dipole antenna formed by the tuning conductor and the dielectric tip member; and
    the dipole antenna configured to radiate electromagnetic energy in at least a radial direction from the dielectric tip member.

2. The applicator of claim 1, further comprising the dielectric tip member having a sharp distal tip that can pierce tissue.

3. The applicator of claim 2, further comprising an insulator coaxially extending between the central conductor and outer conductor, the insulator extending a selected distance beyond the distal most end of the outer conductor.

4. The applicator of claim 3, wherein the ferrule is metal and connected to the outer tube with adhesive.

5. The applicator of claim 1, wherein a proximal most end of the ferrule is a selected distance proximal of the distal most end of the outer conductor.

6. The applicator of claim 5, wherein the ferrule is fixedly attached on opposing respective sides thereof to the dielectric tip member and to the outer tube; and wherein the central conductor comprises the central conductor of a cable extending within the outer tube.

7. The applicator of claim 1, further comprising;
    a fluid conduit connected to a source of cooling fluid via a pumping device; and
    wherein the pumping device is operable, in use, to supply cooling fluid at a predetermined rate to the radiation applicator via the fluid conduit.

8. The applicator of claim 1, wherein the tuning conductor is a metal washer.

9. The applicator of claim 8, wherein the distal end of the central conductor has an abutment wall for receiving the washer.

10. The applicator of claim 1, wherein the applicator operates in the frequency of up to 8 GHz.

11. The applicator of claim 1, wherein the first surface of the ferrule is proximal to the second surface of the ferrule and the second surface of the ferrule is proximal to the third surface of the ferrule.

12. A radiation applicator for applying electromagnetic radiation to tissue, comprising:
    a central conductor having a distal end and a proximal end and adapted to be coupled to a source of electromagnetic radiation;
    a dielectric tip member having a distal end and a proximal end;
    an outer conductor having a distal end and a proximal end, and outer tube having a distal end including a distal most end, and a proximal end, the distal most end of the outer tube ending proximal to a distal most end of the applicator, the outer tube coaxially surrounding the outer conductor such that a gap is formed between the outer conductor and the outer tube, wherein the gap provides a space for a cooling fluid to flow;
    the gap extends from a proximal end of the applicator to a ferrule, the ferrule having a distal end including a distal most end, and a proximal end, the distal most end of the outer tube extending proximally from the distal most end of the ferrule for a selected distance, the ferrule having a first surface, a second surface, and a third surface, the first surface of the ferrule extending coaxially along the outer conductor and the central conductor, the second surface of the ferrule coaxially extends along the distal most end of the outer tube, the third surface of the ferrule having a first point and a second point, the first point of the third surface is in contact with the outer tube and the second point of the third surface is in contact with the outer conductor, the third surface extends between the distal end of the outer conductor and the distal end of the outer tube, the ferrule is spaced between the outer conductor and the outer tube thereby sealing the gap such that the proximal end of the ferrule prevents the cooling fluid from contacting a dipole antenna.

\* \* \* \* \*